(12) United States Patent
Bradford

(10) Patent No.: US 9,345,803 B2
(45) Date of Patent: May 24, 2016

(54) ABSORBENT MATERIAL

(75) Inventor: Colin Bradford, Keighley (GB)

(73) Assignee: ADVANCED MEDICAL SOLUTIONS LIMITED, Winsford, Cheshire (GB)

( * ) Notice: Subject to any disclaimer, the term of this patent is extended or adjusted under 35 U.S.C. 154(b) by 0 days.

(21) Appl. No.: 13/519,029

(22) PCT Filed: Dec. 23, 2010

(86) PCT No.: PCT/GB2010/002326
§ 371 (c)(1),
(2), (4) Date: Jun. 25, 2012

(87) PCT Pub. No.: WO2011/077096
PCT Pub. Date: Jun. 30, 2011

(65) Prior Publication Data
US 2012/0276183 A1     Nov. 1, 2012

(30) Foreign Application Priority Data

Dec. 24, 2009   (GB) .................................. 0922664.8

(51) Int. Cl.
| | | |
|---|---|---|
| *A01N 25/10* | (2006.01) | |
| *B29B 9/00* | (2006.01) | |
| *A01N 59/12* | (2006.01) | |
| *A01N 59/16* | (2006.01) | |
| *A01N 59/20* | (2006.01) | |
| *A61L 15/46* | (2006.01) | |
| *A61L 15/22* | (2006.01) | |

(52) U.S. Cl.
CPC .............. *A61L 15/46* (2013.01); *A61L 15/225* (2013.01); *A61L 2300/102* (2013.01); *A61L 2300/104* (2013.01); *A61L 2300/106* (2013.01); *A61L 2300/206* (2013.01); *A61L 2300/404* (2013.01)

(58) Field of Classification Search
CPC ...................................................... A61L 15/225
See application file for complete search history.

(56) References Cited

U.S. PATENT DOCUMENTS

| 2007/0275043 A1* | 11/2007 | Freeman et al. ............... 424/445 |
|---|---|---|
| 2008/0241229 A1 | 10/2008 | Li et al. |
| 2009/0226391 A1 | 9/2009 | Roberts et al. |
| 2010/0203144 A1 | 8/2010 | Laurencin et al. |

FOREIGN PATENT DOCUMENTS

| CN | 1704510 A | 12/2005 |
|---|---|---|
| CN | 1715465 A | 1/2006 |
| EP | 1859816 | 11/2007 |
| WO | WO 02/085951 | 10/2002 |
| WO | WO 2009/025955 | 2/2009 |

OTHER PUBLICATIONS

International Search Report for PCT/GB2010/002326 mailed May 13, 2011.

* cited by examiner

*Primary Examiner* — Adam C Milligan
*Assistant Examiner* — Sarah Alawadi
(74) *Attorney, Agent, or Firm* — Nixon & Vanderhye P.C.

(57) ABSTRACT

An absorbent product intended particularly for use as a wound dressing comprises an admixture of carboxymethyl chitosan and chitosan wherein the chitosan incorporates at least one antimicrobial agent. Absorbency is provided by the carboxymethyl chitosan and antimicrobial properties by the antimicrobial agent incorporated in the chitosan.

19 Claims, No Drawings

ABSORBENT MATERIAL

This application is the U.S. national phase of International Application No. PCT/GB2010/002326 filed 23 Dec. 2010 which designated the U.S. and claims priority to GB 0922664.8 filed 24 Dec. 2009, the entire contents of each of which are hereby incorporated by reference.

The present invention relates to an absorbent material with antimicrobial properties which is suitable for example, for use as a wound dressing. More particularly, the invention relates to an absorbent product based on chitosan fibres and carboxymethyl chitosan fibres.

Chitosan (1,4)-2-amine-2-dioxy-β-D-glucan and is of the following structure:

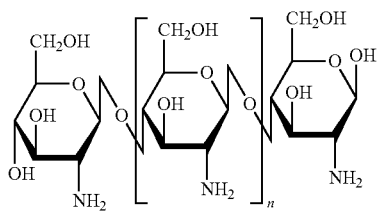

Chitosan is produced commercially by the deacetylation of chitin, which is the structural element in the exoskeleton of crustaceans (crabs, shrimps etc.).

Chitosan has a number of uses such as agriculture, in filtration or clarifying systems. It also has the ability to bind metal ions, including calcium and so has been used as a haemostat.

It is claimed to have antimicrobial properties, and so has been used in clothing and wound dressings.

Chitosan powder can be converted into fibres by a wet spinning process. The chitosan powder is dissolved in dilute acetic acid to form a viscous dope, which is then forced through a plate with fine holes into a solution of sodium hydroxide. Filaments are precipitated in the solution, then washed, dried and cut into fibres.

Once in fibre form, nonwoven fabrics can be produced such as needled felts, or it can be spun into yarns and woven or knitted structures created.

A drawback with chitosan is that it has relative low absorbency, which limits its use where high absorbency is required such as for wound dressings or nappies (diapers).

It is known to produce chitosan fibres (for use in producing a wound dressing) containing silver as an antimicrobial agent. Thus CN1704510A discloses that chitosan fibres with antimicrobial properties may be prepared by spinning a solution of chitosan (in acetic acid) which also contains a water-insoluble silver compound. The preferred silver compound employed in the disclosure of CN1704510A is silver sodium zirconium phosphate, particularly with a particle size less than 1 µm. However such fibres are still of relatively low absorbency.

In the case of cellulose, it is known that carboxymethylation thereof significantly improves the absorbency and gelling characteristics. Similarly, it is also possible to carboxymethylate chitosan fibres to improve absorbency and gelling improvements.

We have however established that it is difficult to produce carboxymethyl chitosan which incorporates an antimicrobial agent. More particularly, we have established that if chitosan fibres containing an insoluble silver compound prepared as disclosed in CN1704510A are carboxymethylated, then the release of silver ions is entirely or almost entirely inhibited, and therefore the fibres do not provide antimicrobial properties. Moreover carboxymethylation of chitosan fibres containing other antimicrobial agents does not necessarily lead to production of a carboxymethyl chitosan with antimicrobial properties. Thus, for example, an antimicrobial agent in chitosan to be carboxymethylated may be "lost" during the carboxymethylation process, e.g. due to water solubility or reaction with reagents used in such a process. More particularly, such a process involves the use of strongly alkaline conditions which cause antimicrobial agents to be released from the chitosan and therefore not able to provide an antimicrobial effect in the carboxymethylated product.

It is therefore an objection of the present invention to obviate or mitigate the above mentioned disadvantages.

According to a first aspect of the present invention there is provided an absorbent product comprising an admixture of carboxymethyl chitosan and chitosan wherein the chitosan incorporates an antimicrobial agent.

According to a second aspect of the present invention there is provided a method of producing an absorbent product comprising the steps of:
(i) providing carboxymethyl chitosan;
(ii) providing chitosan incorporating at least one antimicrobial agent; and
(iii) blending said carboxymethyl chitosan and said chitosan incorporating at least one antimicrobial agent to produce the absorbent product.

The admixture of (i) carboxymethyl chitosan, and (ii) chitosan incorporating at least one antimicrobial agent provides good absorbent properties (provided particularly by the carboxymethyl chitosan) and good antimicrobial properties (as provided by the chitosan incorporating the antimicrobial compound).

A range of antimicrobial agents may be used for the purposes of the invention. Examples include, but are not limited to, metals (and more usually their compounds, e.g. salts) such as silver, copper (particularly copper (I)) and zinc or combinations thereof. Preferred silver, copper and zinc compounds are where the anion is compatible with human use. Examples of suitable anions include chloride, sulphate, phosphate, carbonate, oxide, citrate, iodide. Particular examples of metal compounds that may be used for the purpose of providing an antimicrobial effect include silver citrate, silver sulphate, silver chloride, copper (I) chloride, copper (I) iodide, zinc oxide and combinations thereof. Any combination of the metallic compounds can be used. A further possibility for the antimicrobial agent is iodine and/or its salts. Where the product of the invention incorporates more than one antimicrobial agent then it may be selected from any combination of the aforementioned agents. Furthermore any of a range of organic antimicrobial agents may be used, for which specific examples are given later in the specification.

The admixture of (i) carboxymethyl chitosan, and (ii) chitosan incorporating at least one antimicrobial agent may, for example, be in the form of a powder but is more preferably an admixture of fibres of (i) and (ii). Such fibres are useful particularly for the production of wound dressings since they provide for good absorbency of wound exudate and delivery of an antimicrobial agent to the wound.

A fibrous product in accordance with the invention may for example be a non-woven material (such as a needled felt). Alternatively the fibrous product may be a spun yarn or a woven or knitted structure.

Carboxymethyl chitosan for use in the invention may be produced as disclosed in EP1859816 (A1) in which chitosan fibres are treated with an inorganic alkali such as sodium hydroxide, then as a second step with a salt of a haloacetic acid, such as sodium chloroacetate. Alternatively carboxymethyl chitosan may be produced by the technique disclosed In CN1308510C in which this reaction is performed as a single step. Once this reaction has been completed the carboxymethyl chitosan fibres are washed in aqueous solutions of an organic solvent such as ethanol or acetone, and then dried.

The degree of carboxymethylation to achieve suitable absorbency and gelling is dependent on the method of employed. Some methods produce absorbent, clear gelling fibres in the range 0.3-0.6, whereas in the method described in CN1308510C the level is 0.6-1.2. The degree of carboxymethylation is defined here as the weight ratio of the carboxymethylating agent (e.g. haloacetic acid) to chitosan, eg a degree of carboxymethylation of 0.6 means 600 g of haloacetic acid are used for each kilogram of chitosan fibre. The higher the level of carboxymethylation the greater the level of absorbency and gelling characteristics of the carboxymethyl chitosan. Whilst the degree of carboxymethylation is preferably in the range 0.3-1.2 values outside this range may be used. However, the value should not be so high that the material completely dissolves in an excess of water. Nor should it be so low that its water absorbency and gelling characteristics are inadequate for the intended purpose.

Chitosan fibres incorporating at least one antimicrobial agent for use in the invention may be produced in a number of ways. Thus, for example, the fibres may be produced by spinning a dope containing dissolved chitosan and at least one antimicrobial agent into a precipitation bath so as to produce fibres which incorporate the antimicrobial agent(s). As an alternative, it is possible to produce chitosan fibres by spinning a dope of dissolved chitosan into a precipitation bath and subsequently treating the fibres with an antimicrobial agent. Both possibilities (which may be used in combination) are discussed more fully below.

An insoluble silver compound incorporated in chitosan for use in the invention may be silver sodium zirconium phosphate. As such, fibres as produced in accordance with the disclosure of CN1704510A may be used for the purposes of the invention However, silver sodium zirconium phosphate is not a preferred insoluble silver salt for use in the invention since the amount of silver in silver sodium zirconium phosphate is relatively low. As such, it is necessary to use relatively high amounts of this silver compound in the spinning dope to ensure production of a product from which a sufficient amount of silver may be released to provide the required antimicrobial effect. Adding large quantities of insoluble, non-fibre forming materials to a dope which is to be wet spun can lead to processing problems such as filament breakages. For these reasons, it is preferred that the insoluble silver compound to be incorporated in the chitosan is one having a silver content of greater than 50% by weight. This percentage is calculated on the basis of the chemical formula of the salt but excluding any water of crystallisation. Preferably the water-insoluble silver compound is one that has a solubility constant $K_{SP}$ (at 25° C.) in the range $1\times10^{-5}$ to $1\times10^{-13}$. Compounds with a solubility constant greater than $1\times10^{-5}$ may tend to release silver ions too rapidly, creating an excess and increasing the risk of toxicity. If the solubility constant is less than $1\times10^{-13}$ then the compound may release too few silver ions to be an effective as an antimicrobial agent. For the sake of completeness, Appendix 1 lists the solubility constants of a number of silver compounds.

As indicated above, the amount of silver compound added to a spinning dope must be sufficient to provide the required antimicrobial effect but not so large as to lead to processing problems such as filament breakages. Similar considerations apply to other antimicrobial compounds (e.g. copper and zinc compounds) that are included in a chitosan dope to be spun into fibres.

Chitosan fibres containing an insoluble compound for use in the invention may be prepared by adding the compound into Chitosan dissolved in a dilute (2-3%) acetic acid solution. After a period of degassing (typically 2-7 days) to allow entrapped air bubbles to escape, the dope is spun through a spinneret into a bath of sodium hydroxide solution (~4%), where the chitosan precipitates as continuous filaments referred to as tow. The resulting chitosan filaments contain the antimicrobial compound distributed evenly within each filament. The filaments are subsequently washed, dried and may then be cut into fibres.

As described, the manufacture of chitosan fibres involves washing the tow after the precipitation stage. This is largely to remove residual sodium hydroxide and any other water soluble materials. The final wash is usually an organic solvent such as acetone or alcohol to remove the water from the fibres, making them easier to dry. Materials compatible/soluble in the final wash solution can be added which will then be picked up by the fibres. These additives could be acid to neutralise the fibres, a spin finish to assist in the nonwoven processes, or an antimicrobial agent. This is an alternative way of producing the antimicrobial chitosan fibres. Suitable antimicrobial agents would be iodine, PHMB (polyhexamethylene biguanide), chlorhexidine and groups of antibiotics: Aminoglycosides Ansamycins, Carbacephem, Carbapenems, Cephalosporins, Lincosamides, Macrolides, Monobactams, Nitrofurans, Penicllins, Polypeptides, Quniolones, Sulfonamides, Tetracyclines. The quantity picked up by the fibres would be dependent on the concentration in the solution, and the duration of washing. In the case for iodine, suitable elution levels for effective antimicrobial properties are 1-10 ppm, and typically, 10 times this level would be required in the fibres.

If desired, the chitosan fibres may be treated with EDTA or salt thereof (e.g. a sodium salt) to enhance antimicrobial performance.

Preferred absorbent products in accordance with the invention comprise:
 (i) 55-95% by weight of carboxymethyl chitosan fibres, and
 (ii) 5-45% by weight of chitosan fibres containing the antimicrobial agent(s) ("antimicrobial chitosan fibres").

If the quantity of antimicrobial chitosan fibres (ii) is too high then these fibres will disadvantageously reduce the absorbency and gelling properties of the blended product. If the amount of antimicrobial chitosan fibres (ii) is less than 5% then the antimicrobial properties of the product may be insufficient. Moreover there may be difficulties ensuring an even dispersion and reliable consistency for the blend.

More preferably, the absorbent product of the invention comprises:
 (i) 75-85% (most preferably about 80%) by weight of the carboxymethyl chitosan fibres; and
 (ii) 15-25% (most preferably about 20%) by weight of the antimicrobial chitosan fibres.

The antimicrobial chitosan fibres most preferably contain 1-20% by weight (based on the weight of these fibres) of an insoluble antimicrobial compound, most preferably one containing at least 50% by weight of silver or at least 33% copper. Most preferably the antimicrobial chitosan fibres contain 5-15% by weight (based on the weight of these fibres) of the antimicrobial compound.

Products in accordance with the invention comprising a mixture of (i) carboxymethyl chitosan fibres and (ii) antimicrobial chitosan fibres may be produced using standard techniques. Thus the two fibres types may be blended using common, non-woven techniques.

From the blended fibres, fibrous structures can be created such as needled felts, other nonwovens, or the blended fibres can be spun into yarns and woven or knitted structures created.

A common structure for wound dressings using fibres is a needled felt. The first stage in the production of needled felts is fibre opening. This is the start of the process of separating clumps of fibres into individual fibres. It is at this stage the antimicrobial chitosan fibres and carboxymethyl chitosan fibres would be blended. Weighed quantities of each fibre would be passed into the opener, where blending would take place. Pre-blending by hand can be carried out. Instead of weighing the fibres, this could be done by volumetric means.

The opened, blended fibre is passed to a card where further opening and blending takes place, and a light weight web is produced.

The light weight web is passed to a crosslapper where several layers of web are laid on top of each other to build up the weight.

The layered web is needled to entangle the fibres. This is the repeated penetration of lots of barbed needles attached to a board which entangles the fibres creating the felt. The web can be needled from one side or both sides.

Once needled felt has been produced it can be slit, cut into dressings, packed and sterilised.

The invention is illustrated by the following non-limiting Examples which describe production of (i) carboxymethyl chitosan fibres and (ii) silver chitosan fibres suitable for use in the invention.

EXAMPLE 1

Carboxymethyl Chitosan Fibres

This Example describes the production of carboxymethyl chitosan fibres suitable for use in the invention.

659 g of chitosan tows were wetted with a reaction solution which comprised:

| | |
|---|---|
| Sodium Chloroacetate | 330 g |
| Tween 20 | 26 g |
| Distilled water | 1261 g |
| Sodium hydroxide 8% solution | 1853 g |

The fibres in the tows had a nominal diameter of 2.5 denier, and degree of deacetylation of 90%. The 659 g was made up of 8 tows, each tow being about 130 cm long.

The wetted fibres were then put in fan ovens set at 105° C. for 2 hours.

After reaction, the tows were washed in four stages using the following solutions:

| Wash 1 | |
|---|---|
| Distilled water | 2636 g |
| Acetone | 3259 g |
| Wash 2 | |
| Distilled water | 527 g |
| 1M hydrochloric acid solution | 2109 g |
| Acetone | 3259 g |
| Wash 3 | |

| | |
|---|---|
| Distilled water | 2636 g |
| Acetone | 3259 g |
| Wash 4 | |
| Acetone | 5272 g |
| Tween 20 | 26 g |

The tows were allowed to air dry, and then cut into fibres with a nominal length of 50 mm.

EXAMPLE 2

Silver Chitosan Fibres

This Example describes the production of silver chitosan fibres suitable for use in the invention.

8 g of chitosan powder was dissolved in 20 ml of 36% acetic acid and 400 ml of water.

0.8 g of silver sulphate ground to an average particle size of 2.1 μm was high shear mixed into the dope.

The dope was pumped through a spinneret containing 20 holes each of 150 μm into a bath of 4% sodium hydroxide solution.

The filaments were then washed and dried.

The fibres produced in Examples 1 and 2 were blended using standard techniques and could be converted into a non-woven felt suitable for use as a wound dressing, again using standard techniques.

EXAMPLE 3

Silver Chitosan Sheets

This Example describes the production of a sheet of silver chitosan material. Production of chitosan sheets is an effective way of assessing if an antimicrobial compound is compatible with chitosan, and provides suitable antimicrobial properties. Elution properties and log reduction studies can be performed on the sheets to give an initial assessment of the antimicrobial, and help in determining the appropriate level. It has to remembered that the antimicrobial chitosan will be diluted by admixture with carboxymethyl chitosan in the finished product, and that levels have to be higher to allow for this dilution.

1500 g of chitosan dope was prepared by adding 30 g of chitosan flakes (Deacetylation >90%) to 1470 g of 3% (0.5M) acetic acid. Two days were allowed for the chitosan to fully dissolve and degass.

3 g of silver citrate was added to 97 g of the dope and high shear mixed until uniformly dispersed. A quantity of the dope was poured into a non-stick tray and spread to form a thin sheet. The sheet was completely covered with 4% (1M) sodium hydroxide solution and left for 2 hours. The reaction with the sodium hydroxide causes the sheet to become a very dark brown/black. The sheet was carefully lifted off, and then the reverse side allowed to react for a further 15 minutes. The sheet was washed in water and allowed to dry.

EXAMPLE 4

Copper Chitosan Sheets

This Example describes the production of a sheet of copper chitosan. The procedure of example 3 was followed but using 3 g copper (I) chloride instead of the silver citrate. The dope formed was turquoise in colour. It formed dark brown chitosan sheets when reacted with the sodium hydroxide.

EXAMPLE 5

Iodised Chitosan

This Example demonstrates that soluble antimicrobials could be added to the wash solution of the chitosan fibres, or as a pre-treatment prior to blending with carboxymethyl chitosan fibres. The Example uses iodine but any other soluble antimicrobial could be used.

A bulk solution was prepared where 0.1 g of solid iodine was dissolved in 100 g of denatured ethanol. This equated to a 0.1% (1000 ppm) w/w solution.

1 g of this solution was diluted with 99 g of denatured ethanol to produce a 10 ppm solution. 10 g of chitosan tow was added and soaked in the solution for 3 hours. The tow was hand squeezed dry, and it initially had a golden colour. It was allowed to air dry overnight; the tow had become white in colour again and smelt of iodine. This confirmed iodine had been added to the chitosan fibres.

APPENDIX 1

| Compound | Formula | Solubility Constant |
| --- | --- | --- |
| Silver(I) acetate | $AgCH_3COO$ | $1.94 \times 10^{-3}$ |
| Silver(I) arsenate | $Ag_3AsO_4$ | $1.03 \times 10^{-22}$ |
| Silver(I) bromate | $AgBrO_3$ | $5.38 \times 10^{-5}$ |
| Silver(I) bromide | $AgBr$ | $5.35 \times 10^{-13}$ |
| Silver(I) carbonate | $Ag_2CO_3$ | $8.46 \times 10^{-12}$ |
| Silver(I) chloride | $AgCl$ | $1.77 \times 10^{-10}$ |
| Silver(I) chromate | $Ag_2CrO_4$ | $1.12 \times 10^{-12}$ |
| Silver(I) cyanide | $AgCN$ | $5.97 \times 10^{-17}$ |
| Silver(I) iodate | $AgIO_3$ | $3.17 \times 10^{-8}$ |
| Silver(I) iodide | $AgI$ | $8.52 \times 10^{-17}$ |
| Silver(I) oxalate | $Ag_2C_2O_4$ | $5.40 \times 10^{-12}$ |
| Silver(I) phosphate | $Ag_3PO_4$ | $8.89 \times 10^{-17}$ |
| Silver(I) sulfate | $Ag_2SO_4$ | $1.20 \times 10^{-5}$ |
| Silver(I) sulfite | $Ag_2SO_3$ | $1.50 \times 10^{-14}$ |
| Silver(I) sulfide | $Ag_2S$ | $8 \times 10^{-51}$ |
| Silver(I) thiocyanate | $AgSCN$ | $1.03 \times 10^{-12}$ |

The invention claimed is:

1. A non-woven absorbent product comprising an admixture of
   (i) 75-85% by weight of carboxymethyl chitosan fibres, and
   (ii) 15-25% by weight of chitosan fibres incorporating at least one antimicrobial agent;
   wherein the at least one antimicrobial agent is an insoluble compound and is only present in the chitosan fibres of (ii), said at least one antimicrobial agent being present at a level of 5-20% by weight based on the weight of chitosan fibres of (ii).

2. A product as claimed in claim 1 wherein the carboxymethyl chitosan has a degree of carboxymethylation in the range 0.3-1.4.

3. A product as claimed in claim 1 wherein the insoluble compound is a silver compound.

4. A product as claimed in claim 3 wherein the silver compound has a silver content of greater than 50% by weight as calculated on the basis of the chemical formula of the salt but excluding any water of crystallisation.

5. A product as claimed in claim 1 wherein the insoluble compound is a copper salt.

6. A product as claimed in claim 5 wherein the copper salt has a copper content of at least 33% by weight as calculated on the basis of the chemical formula of the salt but excluding any water of crystallisation.

7. A product as claimed in claim 1 wherein the insoluble compound is a salt of iodine.

8. A product as claimed in claim 1 wherein the chitosan contains EDTA or a salt thereof.

9. A product as claimed in claim 1 which comprises:
   (i) about 80% by weight of the carboxymethyl chitosan fibres, and
   (ii) about 20% by weight of the chitosan fibres containing the said at least one antimicrobial agent.

10. A product as claimed in claim 1 which is a needled felt.

11. A method of producing a non-woven absorbent product comprising an admixture of
    (i) 75-85% by weight of carboxymethyl chitosan fibres, and
    (ii) 15-25% by weight of chitosan fibres incorporating at least one antimicrobial agent;
    wherein the at least one antimicrobial agent is an insoluble compound and is only present in the chitosan fibres of (ii), said at least one antimicrobial agent being present at a level of 5-20% by weight based on the weight of chitosan fibres of (ii), said method comprising the steps of:
    (i) providing said carboxymethyl chitosan fibres;
    (ii) providing said chitosan fibres incorporating said at least one antimicrobial agent; and
    (iii) blending said carboxymethyl chitosan fibres and said chitosan fibres incorporating at least one antimicrobial agent to produce the absorbent product.

12. A method as claimed in claim 11 wherein said chitosan fibres incorporating said at least one antimicrobial agent are prepared by spinning a dope containing dissolved chitosan and an antimicrobial agent into a precipitation bath to produce fibres.

13. A method as claimed in claim 11 wherein said insoluble compound is a silver compound.

14. A method as claimed in claim 13 wherein the silver compound has a silver content of greater than 50% by weight as calculated on the basis of the chemical formula of the salt excluding any water of crystallisation.

15. A method as claimed in claim 12 wherein said insoluble compound is a copper salt.

16. A method as claimed in claim 15 wherein the copper salt has a copper content of at least 33% by weight of copper based on chemical formula of the salt but excluding any water of crystallisation.

17. A method as claimed in claim 11 wherein said chitosan fibres containing said at least one antimicrobial agent are prepared by spinning a dope containing dissolved chitosan into a precipitation bath to form fibres and treating said precipitated fibres with a treatment solution which contains an antimicrobial agent.

18. A method as claimed in claim 17 wherein the antimicrobial agent in said treatment solution is iodine and/or a salt of iodine.

19. A method as claimed in claim 18 wherein said antimicrobial agent in said treatment solution is PHMB.

* * * * *